(12) United States Patent
Harding

(10) Patent No.: US 6,196,073 B1
(45) Date of Patent: Mar. 6, 2001

(54) HAND HELD GOLF BALL COMPRESSION AND SPHERICITY TESTER

(76) Inventor: Marvin L. Harding, 6471 Boca Cir., Boca Raton, FL (US) 33433

(*) Notice: Subject to any disclaimer, the term of this patent is extended or adjusted under 35 U.S.C. 154(b) by 0 days.

(21) Appl. No.: 09/009,470

(22) Filed: Jan. 20, 1998

(51) Int. Cl.[7] ...................................................... G01L 1/00
(52) U.S. Cl. ........................................................ 73/862.381
(58) Field of Search ................................ 73/862.381, 81, 73/37

(56) References Cited

U.S. PATENT DOCUMENTS

| | | | |
|---|---|---|---|
| 4,136,554 | * | 1/1979 | Larson ....................................... 73/81 |
| 5,222,391 | * | 6/1993 | Reenstra .................................... 73/81 |
| 5,372,030 | * | 12/1994 | Prussia et al. ............................. 73/37 |
| 5,511,410 | * | 4/1996 | Sherts ....................................... 73/81 |

* cited by examiner

Primary Examiner—Benjamin R. Fuller
Assistant Examiner—Jewel V. Thompson

(57) ABSTRACT

This invention is a hand held apparatus used to measure the hardness, or compressibility, of a golf ball and also the sphericity, or roundness, of the ball. The apparatus is small enough to be carried in the typical golf bag and easily fits in the normal hand, thus enabling the user to use the apparatus anywhere. A golf ball is inserted into the apparatus and the ball is automatically centered between two opposing plates. One plate is attached to a calibrated spring while the other plate is attached to a screw, which will be used to drive the associated plate against the ball. The screw will be hand turned until a sensing mechanism will be actuated and thus indicate to the user to stop turning. Each ball being tested will be subjected to the same force and therefore compressed an amount determined by it's own hardness. The amount the ball is compressed is related to the commonly accepted ratings found on today's golf balls and the user will be able to read a compression rating directly from a scale located on the body of the apparatus. This invention will also provide capability to measure the diameter of the ball. By measuring the diameter on several axes, the sphericity of the ball can be determined. Obviously, a ball that is sufficiently "out of round" will not fly true.

6 Claims, 2 Drawing Sheets

HAND HELD GOLF BALL COMPRESSION AND SPHERICITY TESTER

BACKGROUND

1. Field of the Invention

This invention relates to a hand held apparatus intended to be used by golfers to measure a golf ball's compressibility, or hardness, and also the sphericity of the ball.

2. Description of Prior Art

The Compression Ratings used for golf balls have been in use since the 1940's and it has become commonly accepted that a rating of 100 is harder than 90. This practice is still the norm for today's balls. Originally, manufacturing methods had difficulty in producing balls with consistent hardness and quality and therefore the testing and rating systems were devised. The manufacturing process produced balls with a wide range of hardness and the harder balls were actually those balls which were produced when the manufacturing process was working at it's best. These balls were considered to be higher quality and were more costly to the golfer. For this reason, harder balls were considered to be better than the softer balls. These balls were manufactured using what is today referred to as a three part construction; a central core, a wound middle core and a soft balata cover.

Previous patents relating to this field are:

U.S. Pat. No. 2,278,416 to Atti (1942). This patent describes a portable test apparatus but is too large to be hand held but can be set up at golf clubs or stores. U.S. Pat. No. 2,628,496 to Wick (1953). This patent describes a hand held apparatus and utilizes a flexible circular ring through which to apply pressure against the ball along the perimeter of the ball and to also gauge sphericity.

U.S. Pat. No. 3,665,757 to Hoag (1972). This patent is an adaptation to the Atti patent but includes a circular go no-go gauge to measure ball sphericity. U.S. Pat. No. 3,653,479 to Phillips (1972). This patent is an adaptation to the Atti patent to all the apparatus to be coin actuated. U.S. Pat. No. 3,665,757 to Valebrach (1985). This patent is designated to be used to measure and sort balls in a manufacturing environment.

All of the above cited patents used the same technique to apply force to the ball under test. This technique was based on having a plate being moved a predetermined and fixed distance against the ball. This movement caused the ball to be forced against an opposing plate which was attached to a calibrated spring. A rod was affixed to this plate and extended back through the spring to contact a stem on a Dial Indicator. As the stem was moved, it rotated the dial pointer and gave a visual reading to the user. These numbers were then used to sort the balls for their rating and became the commonly accepted ratings of 80, 90 and 100. Since the harder balls will compress less than the softer balls, they will move the stem more than the softer balls and will indicate a higher number.

As a result of this technique, there are two variables involved in the testing procedure. The force applied by the spring is a function of it's Spring Rate and the distance it is depressed. This is Hooke's Law and is expressed by Force= Spring Rate×Distance Depressed. Therefore, as the spring is depressed, the force increases against the ball. It is also clear from the previous patents that the harder balls are compressed less than the softer balls. This results in the harder balls compressing the spring more than the softer balls and in turn this creates more force against the harder balls than against the softer balls. Because of this method, the amount of force being applied against the ball under test is variable from ball to ball. The net result is that the hardness of the ball itself plays a role in determining the amount of force being applied and thus affects the test results.

Only the U.S. Pat. No. 2,628,496 to Wick (1953) describes a hand held golf ball tester. This patent also included a method for gauging the diameter of the ball under test by providing a circular ring into which the ball must fit prior to testing. Sphericity of the ball was determined by a visual observation of how the ball fit into the ring. Balls with larger diameters would not fit and could not be tested for hardness. This patent did not provide a direct read out of the ball's compression ratings as used today but referred to the amount of "compressional force in pounds" applied to the ball and the user was left to determine how much force was good or bad.

All these patents were made using metal for the material and had many moving parts, including levers and gears for the homemade dial indicators, except for Atti which used a off-the-shelf Dial Indicator. As a result, these devices were expensive and beyond the price range a typical golfer would care to pay.

The invention described herein is different from previous patents in that the testing is accomplished by applying an identical force against all balls and this force is not a function of the ball's hardness as is the case in the previous patents. This means that the same force is applied against each ball tested and then the amount of ball compression is measured and the rating is indicated directly to the user. A large portion of this device uses modem/high strength plastics and a minimum of moving parts and therefore costs will be within the price range of interest to the average golfer.

The invention described herein is capable of measuring the sphericity of any ball by measuring the ball diameter along any number of axis and therefore the sphericity is easily determined. This invention has a self centering method for the ball and does not require the user to place or hold the ball during testing.

Objects and Advantages

With the availability of new materials and manufacturing techniques, a new type of ball has emerged, called a two piece construction or two part ball. These balls are naturally harder than the three part ball and therefore do not conform to the long accepted ratings of 90 and 100 used for the three part balls. Tests on hundreds of balls of all types, three part and two part, has shown a range of 80 to 150 with the three part balls in the lower range.

Today, a harder ball does not mean better. In fact, it is now known that a golfer should try to match his or her swing speed to the proper ball hardness for optimum feel and distance. This is evidenced by the advertisements being put out by the manufacturers.

Today, there are a number of balls being sold and with many claims for distance, control feel, etc. but the old standards of hardness rating are not longer valid and can not be used to compare balls between different manufacturers or even the different types of construction. This means that a 100 ranting from one manufacturer is not necessarily the same 100 rating from another. Many balls are not even rated.

Golfers do not all have the same swing speeds and therefore do not strike the ball with the same force. Because of this, all golfers do not compress a ball the same amount and therefore some golfers may not be able to compress the ball to its designed maximum compression and consequently will not attain the balls' maximum performance.

Play testing different balls while having a specific rating beforehand as determined by this device means that the golfer will be able to match a specific rating to those balls which provides the optimum performance for their own swing speed. This rating can then be used to evaluate new balls by comparing measured ratings; lower, equal or higher.

It is the intent of this invention to provide the golfer with a modern and accurate tool by which the golfer can measure and/or sort any type of ball and match the ball's hardness to their specific swing speed.

Using this device will provide the capability to sort balls into high, medium or low categories based on hardness thus giving the professional and low handicap players the opportunity to play very tightly controlled balls. Using the device on the course will allow the player to measure and determine when a ball ay have become degraded. "Experienced" and X-OUT balls can be measured and those not meeting the same standards for new balls can be discarded before use. Each golfer will be able to precisely determine which balls have the best feel for their swing speed and therefore use a quantified measure to select balls for future play and therefore eliminate the need to purchase new balls and play test to determine desirability.

Using this device will allow the golfer to also measure the diameter of the ball along a number of different axis and therefore allow the user to measure the sphericity of the ball.

DRAWING FIGURES

DESCRIPTION

Figure 1:
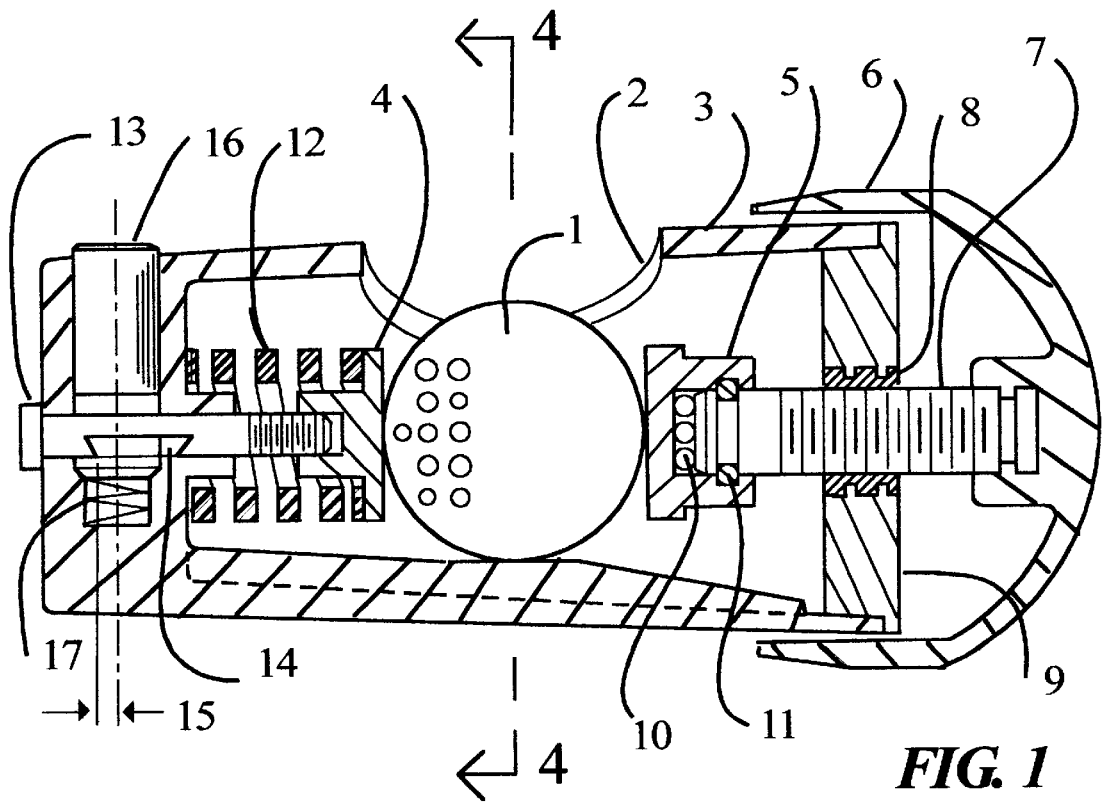
FIG. 1 shows the cross section through the apparatus, including a ball to be tested.
Figure 4:
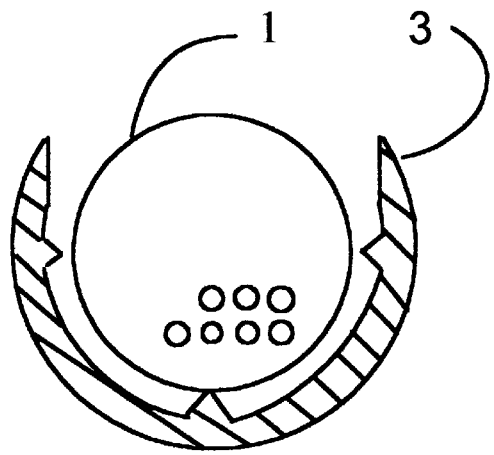
FIG. 4 shows a cross section view of the body showing the self centering technique for the ball.

This device is hand operated and is initiated by placing a ball 1 into the device through the opening 2 (see FIG. 1) located in the top of the body 3. The ball is self centered (see FIG. 4) between two opposing plates, a spring plate 4 and a screw plate 5. These plates are on the same longitudinal axis. Holding the body 3 of the device in one hand, there is a knob 6 located on the other end of the device. The user will turn the knob 6 clockwise until a sensing mechanism is actuated indicating to the user to stop turning. The knob 6 is molded to the shaft 7 which has a threaded portion along it's axis. As the knob 6 is turned, the shaft 7 will turn through a threaded sleeve 8, which is molded into a plastic end cap 9, and this will provide the external force to the ball. The end cap 9 is epoxy sealed to the body 3. On the end of the shaft 7 opposite to the knob 6 will be the screw plate 5. The screw plate 5 fits over the end of the shaft 7. These are steel balls 10 placed between the screw plate 5 and the end of the shaft 7. These balls 10 will allow the shaft 7 to turn freely within the screw plate 5 and prevent the screw plate 5 from turning on the ball 1 during test. The screw plate 5 is retained on the shaft 7 by use of an O-ring 11.

On the side of the ball 1 opposite from the screw plate 5, the spring plate 4 is in contact with the ball 1 and a calibrated spring 12. A spring rod 13 is slipped through a hole at the end of the body 3 and runs through the spring 12 and is attached to the spring plate 4 via threading the spring plate 4 over the spring rod 13. The spring plate 4, the spring 12 and the spring rod 13 are firmly connected and therefore will move together as the ball 1 is forced against the spring plate 4 by the movement of the screw plate 5 which is driven by the knob 6. The spring rod 13 has a notch 14 cut into it's body. One end of this notch 14 is located a fixed distance 15 (see FIG. 1) from the centerline of the indicator button 16. Below the indicator button 16 is a spring 17 which is always under tension and provides a continuous pressure against the indicator button 16. As the spring plate 4 is forced against the calibrated spring 12, the spring rod 13 is moved with the calibrated spring 12 and will reach a point where the end of the notch 14 will clear the diameter of the indicator button 16. This will cause the indicator button 16 to be snapped upward by the spring 17. This will provide both a visual and audio indication to the user to stop turning the knob 6. This sensing technique provides a known and repeatable force against the ball under test since the spring 12 will be compressed the same amount for every test.

A unique feature of this device is the capability to measure the actual amount of compression the ball undergoes during test. This is shown as follows: (Refer to FIG. 1)

$$X(\text{Ball}) = X(\text{Screw Plate}) - X(\text{Spring})$$

where:

X(ball) is the amount of ball 1 compression

X(Screw Plate) is the distance the screw plate 5 moves and equals the number of turns of the Knob 6 times the pitch of the screw on the shaft 7.

X(Spring) is the fixed distance 15 the force spring 12 is compressed.

Using this design feature a scale 18 was designed which is directly related to the amount of ball compression and provides a rating number to the user. For instance, the harder three part balls will require less movement of the X(Screw Plate) than the softer three part balls to move X(Spring) the fixed distance 15.

Figure 2:
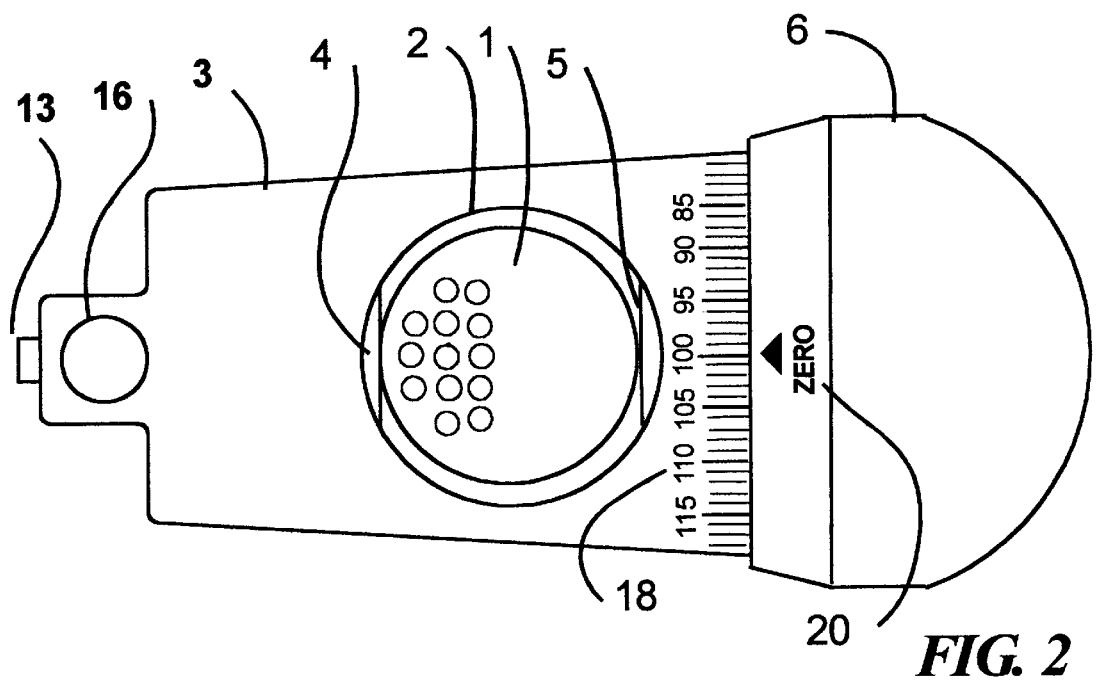
FIG. 2 is a top view and shows the scale and Zero mark located on the Knob in the start position.
Figure 3:
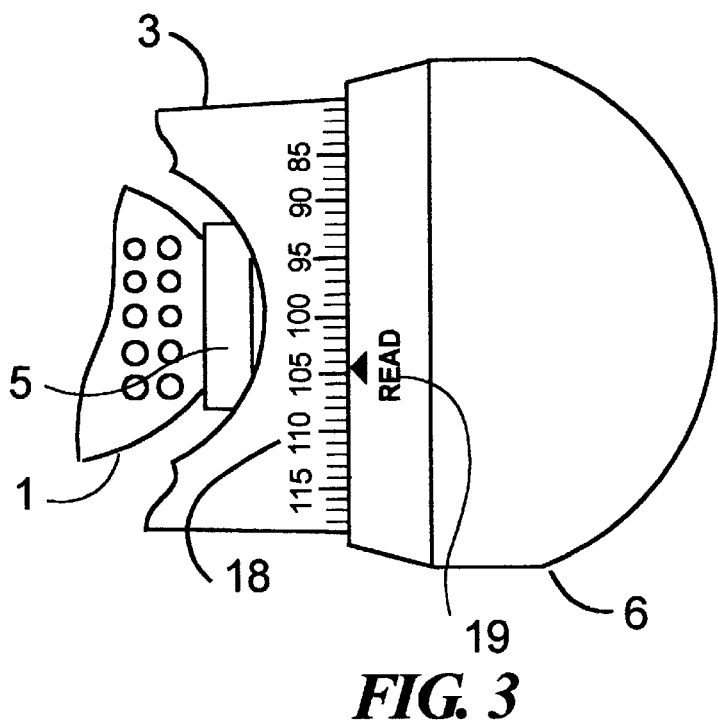
FIG. 3 shows the scale and Read mark located on the Knob and in position to read the compression rating after testing.

The scale 18 is permanently affixed to the body 3, see FIGS. 2 & 3. The scale 18 has been designed to show a number relating to the hardness, or compression, of the ball under test. Using the historical numbers of 100 and 90 as the standard, this scale rates all ball measurements as being relative to the value of 100. The scale 18 has values from 80 to 160 with 80 being the softest value and 160 being the hardest. For historical continuity the device has been designed to use the Titleist Tour Balata 100 as the standard and will read these balls as 100, plus or minus the ball's actual reading.

The knob 6 has a "READ" label 19 located on it's circumference (see FIG. 3). When the indicator button 16 is actuated, then the user can read directly across from the "READ" label 19 to read the hardness value from the scale 18. FIG. 3 shows the device after test and ready to read the hardness rating, in this case a value of 105. After the test is completed, the user only needs to depress the indicator button 16 and turn the knob 6 counterclockwise until the ball is free and roll the ball out of the device. The device is now ready for a new test.

To measure the diameter of a ball simply requires the user to place a ball in the device in the normal fashion. The user may then rotate the knob 6 until there is a snug fit between the screw plate 5 and the spring plate 4. This snug fit is determined by the user feeling the ball 1 to determine that there is a light pressure on the ball 1. (Refer to FIG. 2). The "ZERO" mark 20 on the knob 6 has been calibrated and located to read 100 on the scale 18 when the two plates are separated by a distance of 1.680 inches, which is the standard USGA specification for ball diameter. The user may then read a number from the scale 18. The deviation from 100 will indicate whether the ball is more or less than the standard. Each unit mark on the scale is 0.001 inch. That is, a reading of 105 indicates that the ball diameter is 0.005 inches more than the 1.680 inches while a reading of 95 indicates that the ball is 0.005 less than standard. By measuring a number of diameters, the sphericity of the ball can be determined.

Although the sensing mechanism and scale read out described herein are mechanical means, use of modern microelectronics components and design can be used to accomplish the same end results.

I claim:

1. A hand held apparatus used by golfers to measure hardness, compressibility and sphericity of a golf ball comprising:

a housing having numerical scales, a knob, a spring plate and a screw plate for receiving the golf ball in a central location between said spring plate and said screw plate;

the screw plate being attached to said knob, wherein said knob applies a compression force to the golf ball by rotation of said knob by said golfers;

the screw plate opposing the spring plate and are located on a same longitudinal axis;

a calibration spring and a supporting rod attached to the spring plate; and wherein visual indication of hardness of the golf ball is provided by said numerical scales on said housing.

2. An apparatus according to claim 1, further comprising a shaft, attached to the knob, for moving the golf ball under test towards said calibration spring.

3. An apparatus according to claim 1, further comprising an indicator button located behind the calibration spring, said indicator button being actuated when the calibration spring has been depressed a predetermined amount, providing the same force to the golf ball under test.

4. An apparatus according to claim 3, wherein the indicator button provides an easily visual and audio indication to tell the golfer when to stop applying force.

5. An apparatus according to claim 1, wherein said numerical scales includes an easily visible READ indicator for indicating hardness.

6. An apparatus according to claim 1, wherein said numerical scales includes an easily visible ZERO indicator for indicating sphericity.

* * * * *